US00PP32244P2

(12) United States Plant Patent
Hansen

(10) Patent No.: US PP32,244 P2
(45) Date of Patent: Sep. 29, 2020

(54) ***LAGERSTROEMIA* PLANT NAMED 'PEPPERMINT MOCHA'**

(50) Latin Name: ***Lagerstroemia* (L.) hybrid**
Varietal Denomination: Peppermint Mocha

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/873,023

(22) Filed: Jan. 15, 2020

(51) Int. Cl.
*A01H 5/00* (2018.01)

(52) U.S. Cl.
USPC ..... Plt./252

(58) Field of Classification Search
USPC ..... Plt./252
See application file for complete search history.

*Primary Examiner* — Annette H Para

(57) ABSTRACT

The new and distinct Crape Myrtle plant named *Lagerstroemia* 'Peppermint Mocha' has a dense, broadly-spreading, mounded habit, that is ground hardy to at least USDA zone 6, has glossy, dark-green foliage that have a medium wine-colored blush when young. The rosy-pink flowers on dense reddish stems cover the shrub. The new plant resists leaf spot and powdery mildew and is useful in the landscape as a specimen, en masse, or as a container plant.

1 Drawing Sheet

Botanical classification: *Lagerstroemia* (L.) hybrid.
Variety denomination: 'Peppermint Mocha'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. was on Feb. 1, 2019. Subsequently, on May 29, 2019 Walters Gardens, Inc. advertised the new plant in the "Walters Gardens 19-20 Catalog" followed by the first sale on Jun. 17, 2019. Walters Gardens, Inc. obtained the plant and all information relating thereto, from the inventor. No plants of *Lagerstroemia* 'Peppermint Mocha' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Lagerstroemia* plant, commonly known as Crape Myrtle, and hereinafter referred to by the cultivar name 'Peppermint Mocha' or the "new plant." 'Peppermint Mocha' is grown primarily as an ornamental for landscape use and for use as a potted plant, and is the result of an ongoing breeding program to produce new and improved garden worthy plants for the ornamental plant market. The new plant was the result of open-pollinated seed collected by the inventor in fall of 2012 in a trial garden facility at a wholesale perennial nursery in Zeeland, Mich., USA using the proprietary, unreleased, unnamed hybrid known only by the breeder code H10-08-01 (not patented) as the seed or female parent. The male or pollen parent is a sibling of H10-08-01 (not patented). The new plant was given the breeder code 12-29-3.

*Lagerstroemia* 'Peppermint Mocha' was initially asexually propagated by stem cuttings at a wholesale perennial nursery in Zeeland, Mich., USA in 2014. The resultant plants from successive generations have demonstrated that the new plant has remained stable and true to type in multiple and successive generations of asexual propagation.

SUMMARY OF THE INVENTION

Plants of the new cultivar 'Peppermint Mocha' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Peppermint Mocha'. Among the characteristics in combination which distinguish 'Peppermint Mocha' as a new and distinct cultivar, unique from all other cultivars known to the inventor are:

1. Dense, broadly-spreading, mounded growth habit;
2. Glossy foliage emerges dark green with a medium wine-colored blush and matures to dark-green;
3. Lower stems are striated, reddish-brown and tan-colored with upper stems reddish;
4. Rosy-pink flowers in dense panicles open on new growth to cover the shrub;
5. Resistance to *Cercospora* leaf spot and *Erisphe* powdery mildew;
6. Ground hardy to at least USDA hardiness zone 6.

The most similar cultivars known to the inventor include: 'Chaff Berry' U.S. Plant patent application Ser. No. 16/350,860, 'Dark Roast' U.S. Plant patent application Ser. No. 16/350,861 and the copending U.S. Plant patent application Ser. No. 16/873,024 'Perky Pink'. 'Dark Roast' is slightly shorter in habit, the leaves are deeper reddish purple and the flowers are a different hue of bright fuchsia pink. 'Chaff Berry' is slightly taller and more upright in habit and the flowers are a different hue of rose-pink. 'Perky Pink' has a taller slightly more upright habit and the flowers are a more true pink. The female parent H10-08-01 has flowers that are a more lavender coloration. Comparison with the male parent is not possible since the male parent was not maintained.

BRIEF DESCRIPTION OF THE DRAWINGS

The accompanying color photographs illustrate the flower and foliage characteristics and the overall appearance of a seven-year-old plant of 'Peppermint Mocha', growing in a full-sun trial garden in Zeeland, Mich., showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
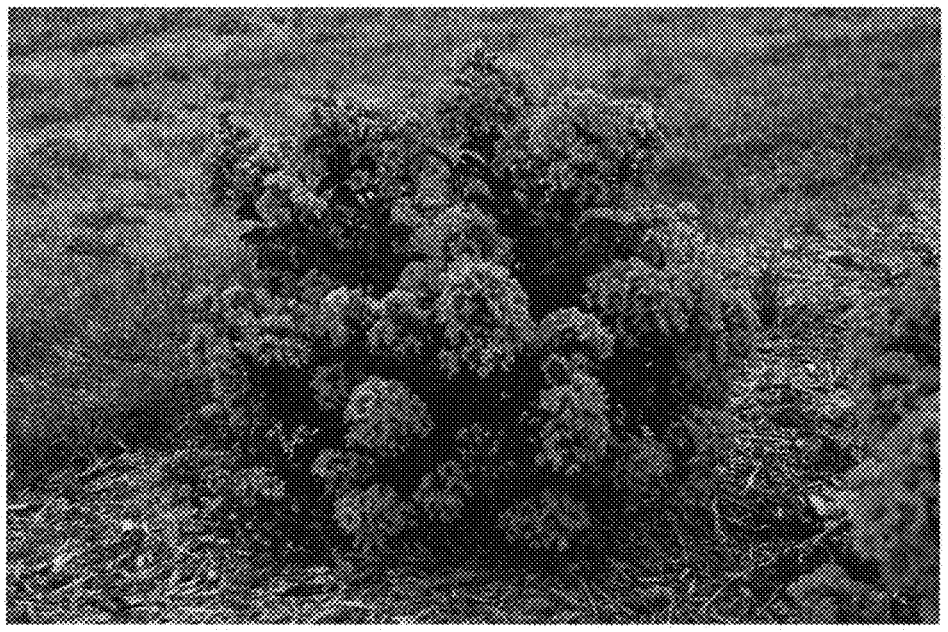
FIG. 1 shows a plant in a full-sun trial garden in late summer peak flowering.
Figure 2:
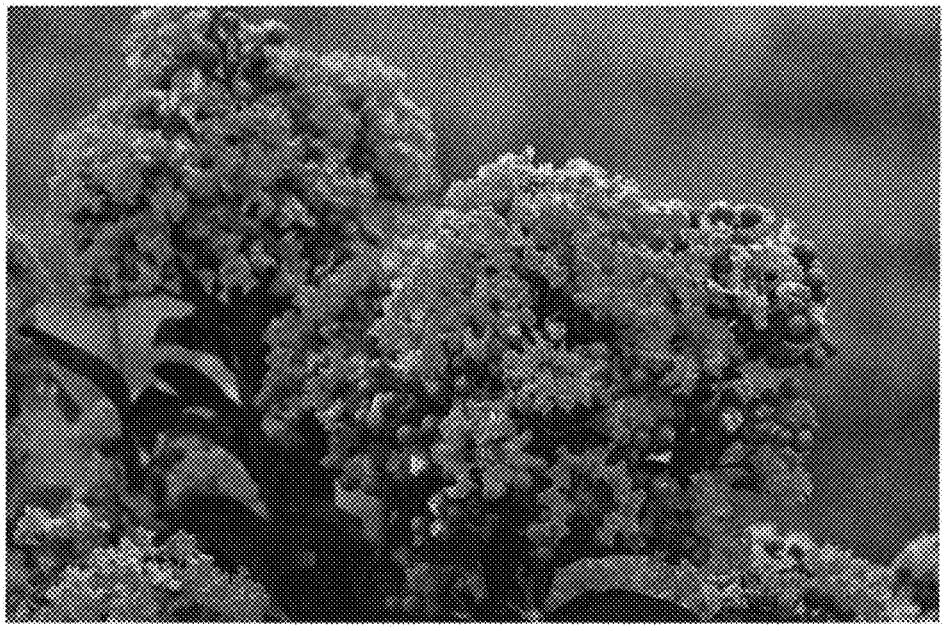
FIG. 2 shows a close-up for the flowers and buds.

The following color references are based on the 2015 edition of The Royal Horticultural Society Colour Chart except where common dictionary terms are used. The following observations and size descriptions are of approximately seven-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* (L.) hybrid;

Parentage: Female, or seed parent the unnamed, unreleased hybrid H10-08-01; the male, or pollen parent is a sibling of H10-08-01;

Propagation: Terminal softwood stem cuttings;

Time to initiate roots: about three weeks;

Growth rate: Moderate; finishing from a 65 mm liner in a 3.7 liter container in about 10 to 14 weeks in the summer season;

Plant description: Deciduous, woody, narrow, compact flowering shrub; about six mainly upright to outward primary stems; freely branched;

Root description: Fine, numerous, fibrous, well-branched;

Plant habit: Broadly-spreading, compact, rounded mound; about 68.0 cm high from the soil level to the top of the inflorescences; about 84.0 cm wide with no pinching, pruning or plant growth regulators;

Stems: About nine; to about 56.0 cm long and about 18.0 mm diameter at base; young stems cylindrical with four longitudinal carinae, along line on either side of petioles; basal stems cylindrical with slightly exfoliating bark; highly branched with about 10 alternate branches held at about a 45 degree angle above horizontal; branches to about 26.0 cm long and 4.0 mm diameter at base;

Stem color: Woody basal portion variable with over wintered stems between RHS 177B and RHS 200A, basal new season stems striated with nearest RHS 176A and RHS 164D; young developing stems striated with nearest RHS 181C and nearest RHS 185A;

Node: About 30 to 40 per main stem; internode length average about 1.5 cm in main stems;

Node color: Same as surrounding stem;

Foliage description: Sub-opposite to alternate; simple; orbicular; margin entire to micro-ciliolate; flat; apex rounded; aequilateral, rounded base; adaxial and abaxial glabrous and lustrous; to about 53.0 mm long and 40.0 mm wide, average about 48.0 mm long and 34.0 mm wide;

Abaxial leaf color: Young emerging adaxial nearest RHS 144A with slight distal blush of nearest RHS 187A, abaxial nearest RHS 146D with moderate blush of nearest RHS 187A; mature adaxial between RHS 137A and RHS NN137A without blush, abaxial between RHS 138A and RHS 146B without blush;

Veins: Pinnate; micro-puberulent adaxial and abaxial;

Vein color: Young emerging adaxial midrib base between RHS 146D and RHS 145A, secondary veins between RHS 144A and RHS 187A, abaxial midrib between RHS 146C and RHS 145B, secondary veins between RHS 144A and RHS 187A; mature adaxial midrib nearest RHS 146D, secondary veins nearest RHS 146B, abaxial midrib nearest RHS 158B and secondary veins nearest RHS 160C;

Petiole: Sessile to very short; glabrous; up to 1.0 mm long and 2.0 mm wide; color adaxial nearest RHS 146B and abaxial nearest RHS 146D with blush of nearest RHS 183D;

Inflorescence: Panicle; terminal branched panicles up to about 200 flowers; average about 175 flowers; up to about 17.0 cm long and about 15.0 cm across; beginning late-summer and continuing for up to four weeks;

Buds: Globose to ellipsoidal; very slightly carinate; with rounded apex and rounded base; lustrous; glabrous; about 12.0 mm long and about 7.0 mm diameter one day prior to opening; longitudinal suture lines of weak prominence;

Bud color: Exposed petals blend between RHS 60C and RHS 64B; calyx base nearest RHS, distally nearest RHS 187B;

Flowers: Perfect; regular; actinomorphic; stalked; held in terminal panicle; individually about 33.0 mm across and about 17.0 mm long to tip of exserted anthers; corolla to about 16.0 mm long; lasting about two days;

Flower fragrance: Faintly sweet;

Peduncle: Cylindrical with four longitudinal carinae in proximal portion and cylindrical in distal portion; about 5.0 mm diameter at base below lowest flowering branch, to about 17.0 cm long and 15.0 cm across;

Peduncle color: Nearest RHS 183C;

Pedicel: Cylindrical; glabrous; lustrous; about 4.0 mm long and 1.0 mm diameter;

Pedicel color: Variable, nearest RHS 183D to RHS N186C;

Calyx: Fused to form hypanthium; campanulate; 9.0 mm long and 10.0 mm across;

Sepals: Fused in about the basal 6.0 mm; acute apex, entire margin; glabrous and lustrous both adaxial and abaxial; about 9.0 mm long and individually and about 4.0 mm wide at fusion point;

Sepal color: Adaxial basal portion nearest RHS NN155B, distal portion nearest RHS 182D; abaxial nearest RHS 183D;

Petals: Six; stalked; glabrous; blade ruffled or crisped; margin crisped; blade with rounded apex and auriculate base, to about 11.0 mm across and 10.0 mm long; claw base or stalk adnate to calyx, to about 6.0 mm long and 0.7 mm diameter; overall about 16.0 mm long;

Petal color: Blade adaxial and abaxial nearest RHS 64C; claw between RHS 51B and RHS 51C;

Androecium:

*Stamens*.—Typically about 40; six longer and about 34 shorter.

*Filaments*.—Cylindrical; shorter stamens to about 8.5 mm long and about 0.2 mm diameter, curved to twisted; longer filaments arcuate in distal 5 mm, about 16.0 mm long and about 0.5 mm diameter; color of shorter filaments nearest RHS NN155D proximally and nearest RHS NN155C distally; color of longer filaments between RHS 51B and RHS 51C.

*Anthers*.—Dorsifixed; ellipsoid; more developed on longer stamens to about 1.5 mm long and 1.2 mm across, on shorter stamens about 1.0 mm long and about 0.7 mm across color nearest RHS 8A.

*Pollen*.—Abundant on longer stamens; color nearest RHS 14A.

Gynoecium: One; about 17.0 mm long;

*Style*.—Cylindrical; glabrous; about 14.5 mm long and 0.5 mm diameter; color nearest RHS 53B.

*Stigma*.—Globose; lustrous; about 0.5 mm diameter; color between RHS 177A and RHS 177B.

*Ovary*.—Superior; globose; lustrous; about 2.0 mm tall and 1.5 mm diameter; color between RHS 153D and RHS 154D.

*Fruit*.—Globose; dehiscent, loculicidal, penta-valved capsule; about 7.0 mm across and 8.0 mm tall; immature color nearest RHS 145C, mature color nearest RHS 165A.

Seed: Typically 12 to 20 seeds per fruit; winged; to about 6.0 mm long and 3.5 mm across and 1.5 mm thick at embryo; color variable, nearest RHS 199B at embryo and RHS 199D in wing;

Disease resistance: *Lagerstroemia* 'Peppermint Mocha' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

It is claimed:

1. A new and distinct cultivar of Crape Myrtle, *Lagerstroemia* plant named 'Peppermint Mocha' essentially as herein illustrated and described.

* * * * *